(12) United States Patent
Ouchi et al.

(10) Patent No.: US 7,674,430 B2
(45) Date of Patent: Mar. 9, 2010

(54) AUTOMATED ANALYZER

(75) Inventors: Katsumi Ouchi, Tokyo (JP); Hiroshi Mitsumaki, Tokyo (JP)

(73) Assignee: Hitachi, Ltd. (JP)

( * ) Notice: Subject to any disclaimer, the term of this patent is extended or adjusted under 35 U.S.C. 154(b) by 112 days.

(21) Appl. No.: 11/447,012

(22) Filed: Jun. 6, 2006

(65) Prior Publication Data

US 2007/0224083 A1 Sep. 27, 2007

(30) Foreign Application Priority Data

Mar. 23, 2006 (JP) ............................. 2006-081035

(51) Int. Cl.
*G01N 35/00* (2006.01)
*G01N 35/10* (2006.01)

(52) U.S. Cl. .................... 422/67; 422/63; 422/64; 422/65; 436/47; 436/48; 436/49

(58) Field of Classification Search .............. None
See application file for complete search history.

(56) References Cited

U.S. PATENT DOCUMENTS

| | | | |
|---|---|---|---|
| 5,149,501 A | | 9/1992 | Babson et al. |
| 5,424,212 A | * | 6/1995 | Pinsl-Ober et al. ............ 436/50 |
| 6,375,898 B1 | | 4/2002 | Ulrich |
| 2003/0028355 A1 | * | 2/2003 | Minati et al. ................ 702/188 |
| 2007/0231208 A1 | * | 10/2007 | Tanaka et al. ................ 422/67 |
| 2008/0019868 A1 | * | 1/2008 | Okumoto et al. ............. 422/63 |
| 2008/0050280 A1 | * | 2/2008 | Fujita .......................... 422/67 |

FOREIGN PATENT DOCUMENTS

| | | |
|---|---|---|
| DE | 43 12 093 | 10/1993 |
| EP | 1 691 201 | 8/2006 |
| JP | 05-232123 | 9/1993 |
| JP | 2000-258430 | 9/2000 |

* cited by examiner

*Primary Examiner*—P. Kathryn Wright
(74) *Attorney, Agent, or Firm*—Antonelli, Terry, Stout & Kraus, LLP.

(57) ABSTRACT

The performance of an analyzer is checked on by use of a performance check cartridge which has the same external shape as a reagent cartridge for analyzing samples has; the performance check cartridge holds reagents for checking on the performance of the analyzer, and concurrently holds process conditions and determination conditions for checking on the performance of the analyzer in the form of two-dimensional dot codes; in accordance with the process conditions recorded in the performance check cartridge, the automated analyzer determines the absorbance by use of the reagents filled in the performance check cartridge, and compares a result of the determination with the determination conditions recorded in the performance check cartridge, thereby checking on the performance of the analyzer.

7 Claims, 12 Drawing Sheets

AUTOMATED ANALYZER

CLAIM OF PRIORITY

The present application claims priority from Japanese application JP 2006-081035 filed on Mar. 23, 2006, the contents of which is hereby incorporated by reference into this application.

BACKGROUND OF THE INVENTION

1. Field of the Invention

The present invention relates to an automated analyzer capable of automatically performing a plurality of assays on a specimen collected from a subject.

2. Description of the Prior Art

As apparatuses each for analyzing a specimen, such as urine and blood, collected from a patient and for thus providing data for a diagnosis by a doctor, there are automated analyzers. A type of automated analyzer is described in JP-A-Hei. 5-232123. This type of automated analyzer makes determination respectively of a plurality of types of samples of a patient which are set in a rack provided with the ID number of the patient. The automated analyzer combines determined data from a plurality of assays, and logically checks on the data. Thereby, the automated analyzer detects a malfunction of the analyzer and an abnormality of the patient while separating the malfunction and the abnormality from each other. Another type of automated analyzer is described in JP-A-2000-258430. This type of automated analyzer holds a plurality of specimens each with a specimen ID in each of specimen racks each with a rack ID. The automated analyzer reads the specimen IDs and the rack IDs, and thus transfers each of the racks to an analysis module corresponding to a requested assay. In each of the analysis modules, a specimen sample and a reagent are pipetted into a reaction vessel, and thereby a determination is made. JP-T-2002-503346 describes an analysis system which includes a plurality of chambers or cuvettes, and which uses a system reagent carrier.

SUMMARY OF THE INVENTION

In the case of the automated analyzer described in JP-A-Hei. 5-232123, an analysis is made by causing a dispenser to transfer a reagent, which has been beforehand prepared in a refrigerated storage, to a sample set in a reaction disc, and to mix the reagent and the sample with each other. For this reason, reagents in number and amount corresponding to assays have to be prepared in the refrigerated storage. If many assays are intended to be performed, a larger-sized cooling box is needed. Accordingly, the analyzer has to be larger in size. The automated analyzer described in JP-A-2000-258430 does not perform a plurality of assays respectively by use of a plurality types of specimens collected from a single patient. Although JP-T-2002-503346 discloses the system reagent carrier including a plurality of chambers or cuvettes, JP-T-2002-503346 discloses no details of an analysis method using the system reagent carrier.

An object of the present invention is to provide an automated analyzer capable of performing a larger number of assays through a simpler operation and with higher reliability.

The automated analyzer according to the present invention checks on the performance of the analyzer by use of a performance check cartridge which has the same external shape as a reagent cartridge for analyzing samples has. The performance check cartridge holds reagents for checking on the performance of the analyzer, and concurrently holds process conditions and determination conditions for checking on the performance of the analyzer in the form of two-dimensional dot codes. In accordance with the process conditions which have been recorded in association with the performance check cartridge, the automated analyzer determines the absorbance by use of the reagent filled in the performance check cartridge. The automated analyzer compares a result of the determination with the determination conditions which have been recorded in association with the performance check cartridge, and thereby checks on the performance of the analyzer. In a case where it is evaluated that there is no problem with the performance of the analyzer through the checking on the performance of the analyzer by use of the performance check cartridge, the automated analyzer enables the samples to be analyzed. In a case where it is evaluated that the performance decreases so that normal analyses cannot be performed, the analyzer shuts itself down in order not to analyze the samples.

In the case of the present invention, the use of the cartridge specialized for checking on the performance makes it possible to simply check on the performance of the entire system, which cannot be evaluated by conventional types of mechanical checks or electrical checks, through a method similar to that with which a regular analysis operation is performed. In addition, the recording of threshold information serving as criteria for the performance check in the cartridge brings about advantages. The advantages include an advantage that a user need not input the information, and an advantage that the setting of the automated analyzer need not be changed when specifications of the cartridge specialized for checking on the performance, including components of a solution, are intended to be changed.

DESCRIPTION OF THE PREFERRED EMBODIMENT

Figure 1:
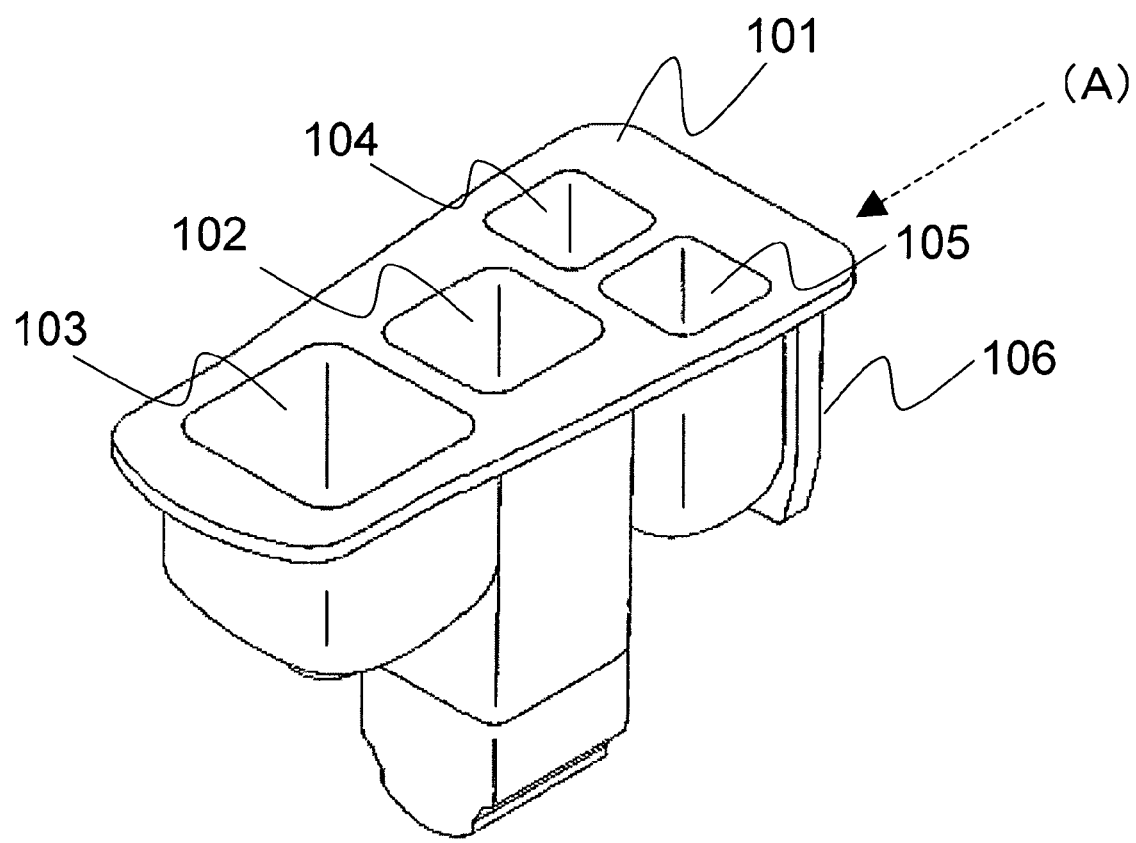
FIG. 1 is a perspective view showing an example of a reagent cartridge.
Figure 2:
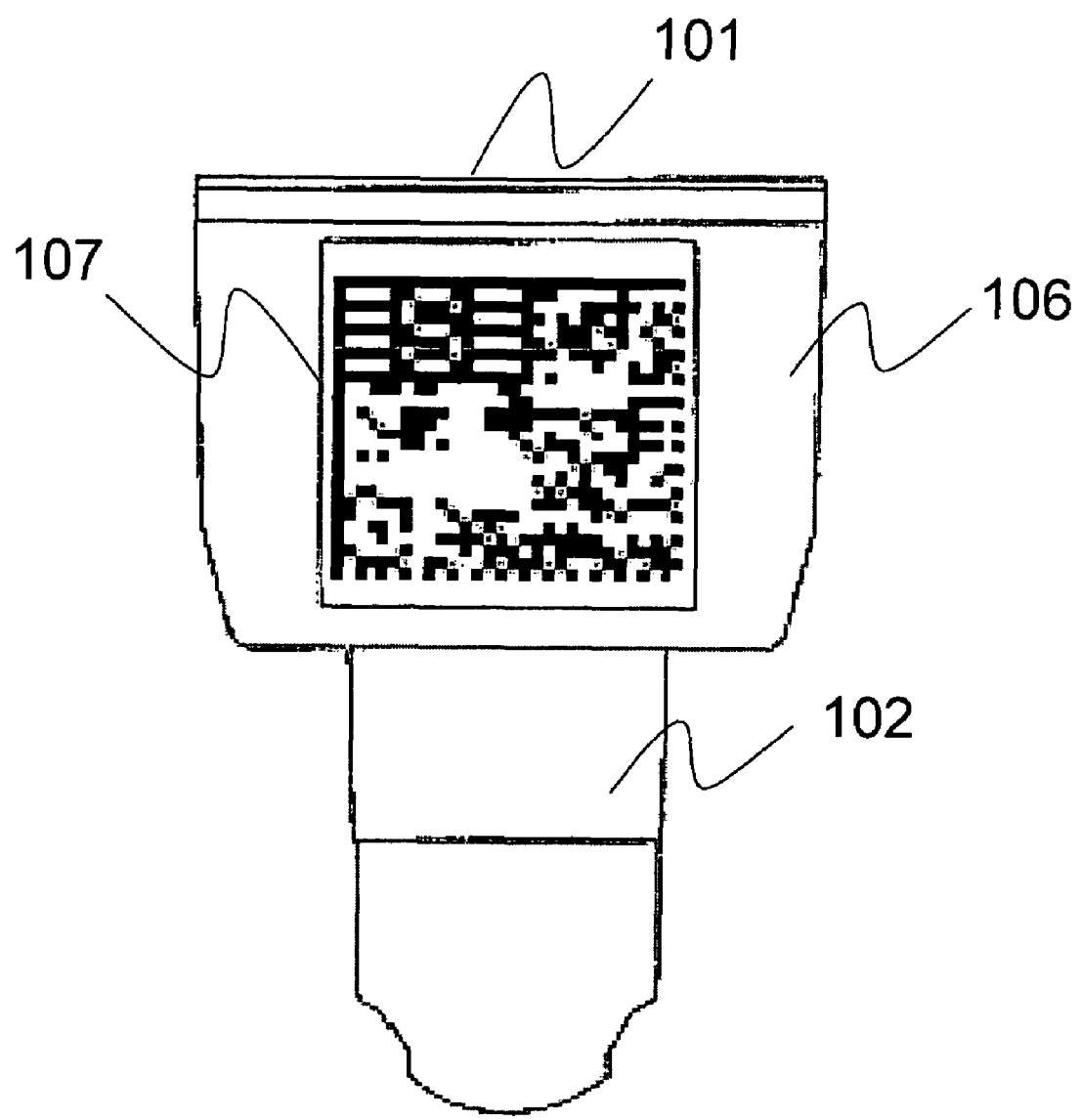
FIG. 2 is a side view of the reagent cartridge.

Hereinafter, descriptions will be provided for an automated analyzer according to the present invention by referring to the drawings. FIG. 1 is a perspective view showing an example of a reagent cartridge used in the automated analyzer according to the present invention. FIG. 2 is a side view which the reagent cartridge looks like when viewed in the (A) direction of FIG. 1.

The reagent cartridge 101 is made, for example, of polypropylene. In the case of the illustrated example, the reagent cartridge is provided with one photometric cuvette and three reagent cuvettes. Reference numeral 102 denotes the photometric cuvette; 103, a first reagent cuvette; 104, a second reagent cuvette; and 105, a third reagent cuvette. The reagent cartridge 101 according to this example includes the first to the third cuvettes. A reagent cartridge according to any other example may be configured to have a new second cuvette which is obtained by integrally forming the second cuvette and the third cuvette. The photometric cuvette 102 is empty before an analysis is carried out. After the automated analyzer pours a sample and reagents into the photometric cuvette and agitates the sample and the reagents therein, the analysis is performed by use of a photometric unit.

In a case where it is one kind of reagent that is needed for the analysis, the same reagent is placed in each of the first reagent cuvette 103 and the second reagent cuvette. In a case where it is two kinds of reagents that are needed for the analysis, the two types of reagents are placed respectively in the first reagent cuvette 103 and the second reagent cuvette 104. In a case where it is three kinds of reagents that are needed for the analysis, the three kinds of reagents are placed respectively in the first reagent cuvette 103, the second reagent cuvette 104 and the third reagent cuvette 105.

In the case of the reagent cartridge 101, reagents needed respectively for an assay with the reagent cartridge are beforehand poured respectively in the reagent cuvettes, and the photometric cuvette 102 is empty. In that state, the entire upper surface of the reagent cartridge 101 is sealed by a sealing label. An assay conducted by use of the reagent cartridge is typed on the sealing label. For example, "TP" is typed on the sealing label of a reagent cartridge for analyzing total proteins. "GLU" is typed on the sealing label of a reagent cartridge for analyzing glucose. "UA" is typed on the sealing label of a reagent cartridge for analyzing uric acid. In addition, sealing labels are marked respectively with colors corresponding to kinds of specimens needed for analyses. For example, the sealing label of a reagent cartridge for which serum is used as a sample is marked with yellow. The sealing label of a reagent cartridge for which urine is used as a sample is marked with green. The sealing label of a reagent cartridge for which whole blood is used as a sample is marked with red. The sealing label of a reagent cartridge for which any other specimen is needed is marked with blue. Such coloration makes it easy for a user to prepare specimen samples needed for an analysis.

The reagent cartridge 101 is used as a cartridge for checking on the performance of the automated analyzer as well. In the case of the performance check cartridge, for example, the reagent cartridge 101 is sealed with a sealing label affixed to the entire upper surface thereof while the first reagent cuvette 103 contains 250 µl of a 0.1N—NaOH solution, the second reagent cuvette 104 contains 100 µl of a 4-nitrophenol/0.1N—NaOH solution, and the photometric cuvette 102 is empty. "CHECK" is typed on the sealing label. The sealing label is marked with no color, and is transparent. In addition, two types of performance check cartridges may be prepared with 4-nitrophenol/0.1N—NaOH solution having a different concentration with each other in each second reagent cuvette. At this time, the absorbances of the two 4-nitrophenol/0.1N—NaOH solutions are 2.5 Abs and 5.0 Abs. In other words, the 4-nitrophenol/0.1N—NaOH solution may be of at least two concentrations for a plurality of performance check cartridges. In a case where two performance check cartridges are prepared, "CHECK1" and "CHECK2" are typed on the transparent and colorless sealing labels respectively of the two cartridges.

A label 107 on which a dot code (two-dimensional code) as shown in FIG. 2 has been printed is affixed to a rear panel 106 of each of the reagent cartridges. The dot code functions as an information recording unit. The following pieces of information are codified, and are stored respectively in predetermined positions in the dot code label 107:

(1) the year and date of production and the expiration date;
(2) the serial number;
(3) the type of a specimen needed as a sample;
(4) the amount of a sample needed and the timing for pipetting;
(5) the amount of a first reagent needed and the timing for pipetting;
(6) the amount of a second reagent needed and the timing for pipetting;
(7) the amount of a third reagent needed and the timing for pipetting;
(8) a photometry method;
(9) the photometric timing;
(10) a primary wavelength and a secondary wavelength for the photometry;
(11) a transformation from the absorbance to the concentration; and
(12) the type of analysis (information for discriminating between the regular analysis and the performance check).

In addition to the above-mentioned pieces of information, the following pieces of information are codified, and are stored in a dot code label of the reagent cartridge 101 used as the cartridge for checking on the performance of the automated analyzer:

(13) the upper limit value, or the upper threshold value, of the absorbance difference;
(14) the lower limit value, or the lower threshold value, of the absorbance difference;
(15) the upper limit value, or the upper threshold value, of the ratio among the absorbance differences, which is observed when two or more kinds of performance check cartridges are going to be used; and
(16) the lower limit value, or the lower threshold value, of the ratio among the absorbance differences, which is observed when the two or more kinds of performance check cartridges are going to be used.

These pieces of information are read by a dot code reading unit inside the automated analyzer, and are stored in a RAM also inside the automated analyzer. The recording of these pieces of information in the cartridge instead of the analyzer brings about the following advantages. The advantages include an advantage that information need not be inputted by a user, an advantage that the setting of the automated analyzer need not be changed when specifications of the cartridge is intended to be changed, and an advantage that the controlling of the information is simplified so that the throughput is improved.

The reagent cartridge 101, whose upper surface is made hermetic with the sealing label, is stored in a refrigerator before the reagent cartridge 101 is used for an analysis. The reagent cartridge is disposable. After the analysis is completed, a user detaches the cartridge, which includes the solution, from the automated analyzer, and disposes of the cartridge.

Figure 3:
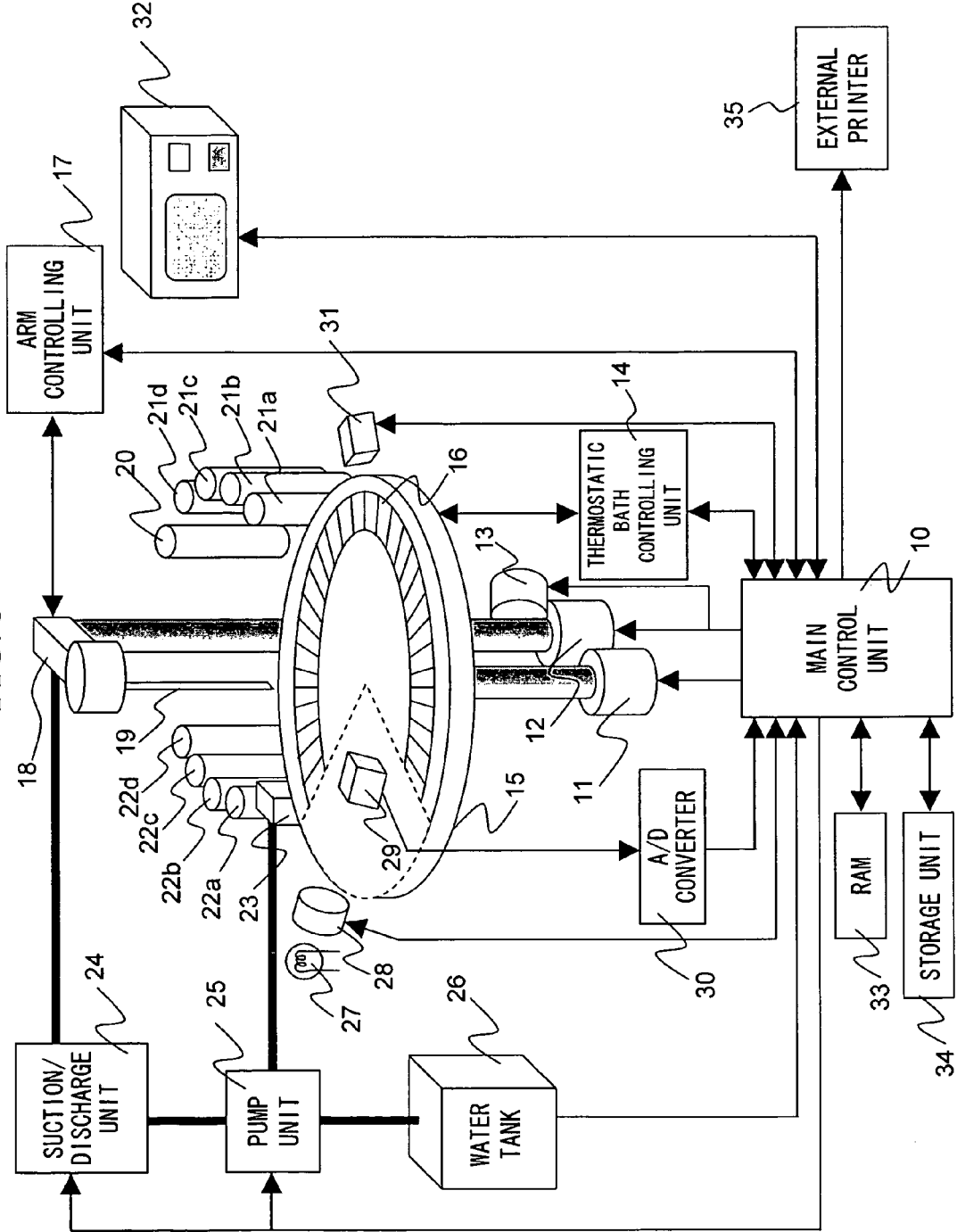
FIG. 3 is a schematic diagram showing an example of an overall configuration of an automated analyzer according to the present invention.
Figure 4:
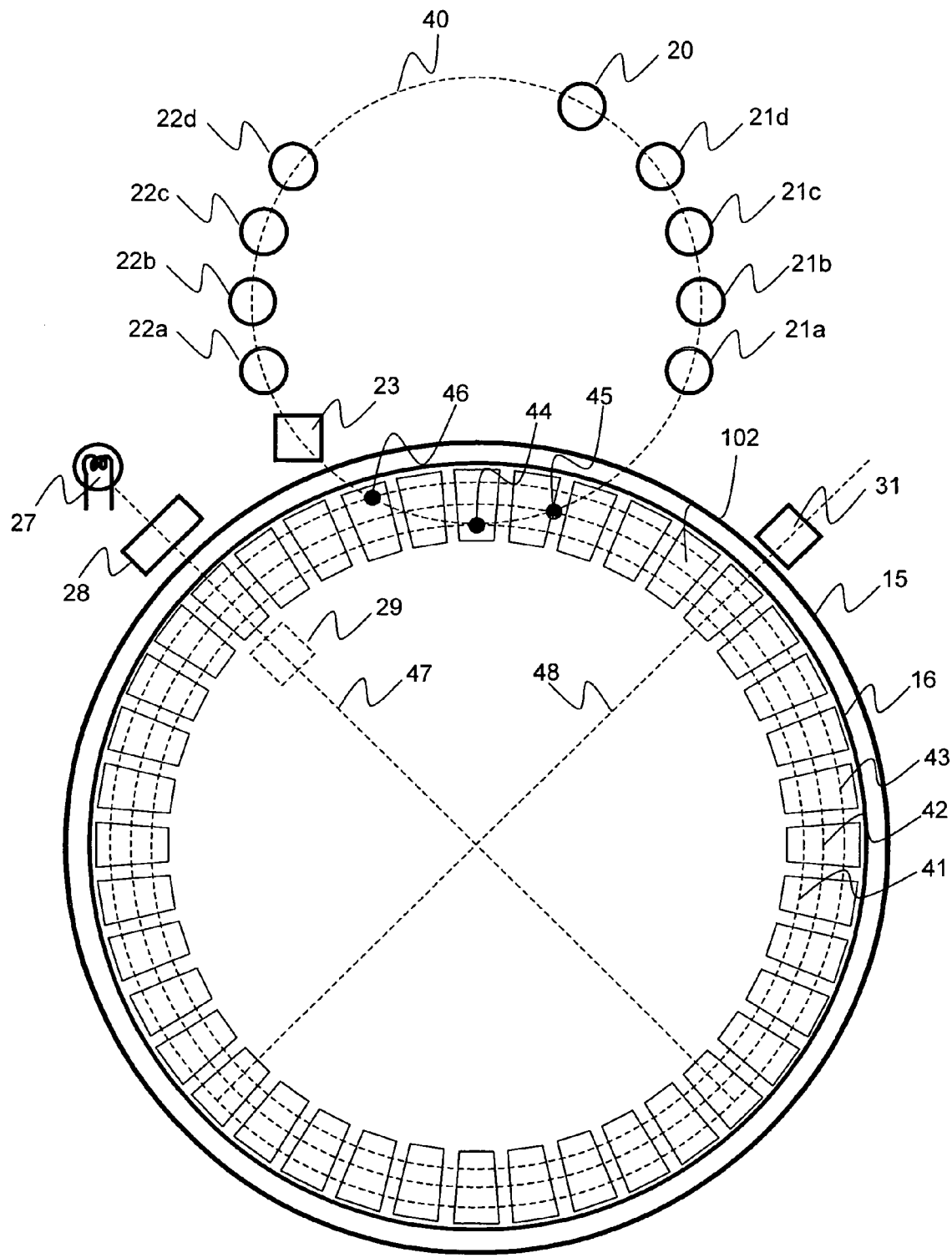
FIG. 4 is a schematic plan view of the automated analyzer according to the present invention.

Descriptions will be provided below for the automated analyzer according to the present invention by use of FIGS. 3 and 4. FIG. 3 is a schematic diagram showing an example of an overall configuration of the automated analyzer according to the present invention. FIG. 4 is a schematic plan view of the example thereof.

The automated analyzer is connected to a commercial power supply. When the power supply switch (not illustrated) is turned on, the power supply is applied to the automated analyzer. A main control unit 10 controls all of the operations of the automated analyzer. The main control unit is configured chiefly of a CPU, a ROM and a real-time clock. A RAM 33 is connected to the main control unit 10, and the RAM serves as a temporary storage memory to which the main control unit 10 makes reference.

A rotor 16 serving as a carrier for the reagent cartridges 101 is provided inside a thermostatic bath 15. A heater is installed in the thermostatic bath 15. The temperature of air inside the thermostatic bath 15 is kept at 37° C. by a thermostatic bath controlling unit 14. The rotor 16 is capable of being rotated through controlling a step motor 11. 40 reagent cartridges at maximum can be mounted in the rotor 16 in the circumferential direction thereof. Each of the reagent cartridges is set in the rotor 16 in a way that its rear panel 106 to which the dot code label 107 is affixed faces to the outer periphery of the rotor 16.

An arm 18 is moved upward and downward by a vertical motion controlling step motor 13, and is capable of being rotated in the horizontal plane by a rotation controlling step motor 12. A probe 19 extending downward in the vertical direction is attached to the extremity of the arm 18. Samples and cleaning fluids are chiefly sucked into, or discharged from, the probe 19. The extremity of the probe 19 is acute in angle like a syringe needle in order that the extremity of the probe 19 may penetrate through the sealing labels with which the photometric cuvette 102 and the reagent cuvettes 103, 104 and 105 are sealed. A heater (not illustrated) is fitted to the probe 19, and thus the probe 19 is kept at a temperature of 37° C. by an arm controlling unit 17. The probe 19 is also used for detecting a liquid level. The liquid level is detected by the arm controlling unit 17 sensing a change in electrostatic capacity between the probe 19 and the ground potential. This function is used for checking on the amounts of the samples and the cleaning fluids. If the arm controlling unit 17 detects the fluid level of each of the samples and the cleaning fluids while the probe 19 is descending, the arm controlling unit 17 transmits a detection signal to the main control unit 10. Reference numeral 20 denotes a housing serving as the home position of the probe 19.

Reference numerals 21*a* to 21*d* denote sample containers. The sample containers are arranged in the circumference 40 whose radius is the horizontal distance between the rotation axis of the arm and the probe 19. Sample containers 21*a* to 21*d* are identified by the main control unit 10 using positional information assigned to each of the sample containers. Positional Information on a container which contains a sample needed by the reagent cartridge is stored in the dot code. The sample containers 21*a* to 21*d* are marked with the same colors as the sealing labels affixed to the reagent cartridges are marked with, the colors respectively indicating kinds of specimens needed. For example, reference numeral 21*a* denotes a sample container for serum or plasma, and the sample container 21*a* is marked with yellow. Reference numeral 21*b* denotes a sample container for whole blood, and the sample container 21*b* is marked with red. Reference numeral 21*c* denotes a sample container for urine, and sample container 21*c* is marked with green. Reference numeral 21*d* denotes a sample container for any other kind of specimen, and the sample container 21*d* is marked with blue. The sample containers 21*a* to 21*d* are capable of being detached from the automated analyzer. Positions in which the corresponding sample containers are disposed are marked with the same colors as the corresponding containers are marked with. Thereby, a user can avoid disposing the sample containers in wrong positions.

Reference numerals 22*a* to 22*d* denote cleaning fluid containers. The cleaning fluid containers are arranged in the circumference 40 whose radius is the horizontal distance between the rotation axis of the arm and the probe 19. The cleaning fluid containers 22*a* to 22*d* are capable of being detached from the automated analyzer. Positions in which the corresponding cleaning fluid containers are disposed are marked with the same colors as the corresponding containers are marked with. Thereby, a user can avoid disposing the cleaning fluid containers in wrong positions.

Reference numeral 44 denotes a first reagent suction unit. The first reagent suction unit 44 is located in a contact point between a circumference 41 and a circumference 40. The circumference 41 passes through the center of each of the first reagent cuvettes respectively of the reagent cartridges. The circumference 40 has a radius which is the horizontal distance between the rotation axis of the arm and the probe 19. When a first reagent contained in the first reagent cuvette of one of the reagent cartridges is going to be sucked by the probe 19, the rotor 16 is rotated, and thus the center of the first reagent cuvette of a targeted reagent cartridge is positioned at the suction unit 44 before the reagent is sucked.

Reference numeral 45 denotes a suction/discharge unit for the photometric cuvette 102 of each of the reagent cartridges 101. The suction/discharge unit 45 is located at an intersection point between a circumference 42 and the circumference 40. The circumference 42 passes through the center of the photometric cuvette 102 of each of the reagent cartridges. The circumference 40 has the radius which is the horizontal distance between the rotation axis of the arm and the probe 19. When a sample and a reagent are going to be discharged from the probe 19 to the photometric cuvette 102 of a reagent cartridge 101, or to be sucked from the photometric cuvette 102 of the reagent cartridge 101 into the probe 19, the rotor 16 is rotated, and thus the center of the photometric cuvette 102 of the targeted reagent cartridge 101 is positioned at the suction/discharge unit 45 before the suction/discharge.

Reference numeral 46 denotes a suction unit for a second and a third reagents. The suction unit 46 is located at an intersection point between a circumference 43 and the circumference 40. The circumference 43 passes through the centers respectively of the second reagent cuvette 104 and the third reagent cuvette 105 of each of the reagent cartridges 101. The circumference 40 has the radius which is the horizontal distance between the rotation axis of the arm and the probe 19. When the second reagent contained in the second reagent cuvette of one of the reagent cartridges is going to be sucked by the probe 19, the rotor 16 is rotated, and thus the center of the second reagent cuvette 104 of the targeted reagent cartridge is positioned at the suction unit 46, before the reagent is sucked. In addition, when the third reagent contained in the third reagent cuvette of one of the reagent cartridges is going to be sucked by the probe 19, the rotor 16 is rotated, and thus the center of the third reagent cuvette 105 of the targeted reagent cartridge is positioned at the suction unit 46, before the reagent is sucked.

The thermostatic bath 15, the rotor 16, the arm 18, the probe 19, the housing 20, the sample containers 21*a* to 21*d*, and the cleaning fluid containers 22*a* to 22*d* is covered with a lid (not illustrated) which is capable of being opened and closed. A heat insulating material attached to the lid covers over the thermostatic bath 15, and thus has an effect of keeping the temperature of the air in the thermostatic bath 15 constant. A switch for detecting the opening of the lid and a lid locking mechanism (none of the two is illustrated) are installed respectively in vicinities of the lid. When the lid is opened, the switch for detecting the opening of the lid is turned on, and thus transmits a detection signal to the main control unit 10. In addition, the lid is capable of being locked by the lid locking mechanism being operated by control from the main control unit 10. The lid is always locked during an analysis operation.

A cleaning station 23 is a place where the inside and outside of the probe 19 are cleaned. When a cleaning is going to be carried out by use of purified water, purified water is discharged from the inner wall of the cleaning station 23 by the driving of a pump unit 25, and thus the outside of the probe 19 is cleaned. Concurrently, purified water is discharged from the inside of the probe 19 by the driving of the suction/discharge unit 24 and the pump unit 25, and thus the inside of the probe 19 is cleaned. Furthermore, when a cleaning is going to be carried out by use of cleaning fluids, the probe 19 sucks cleaning fluids respectively from the cleaning fluid containers 22a to 22d, and discharges the sucked cleaning fluids into the inside of the cleaning station. Waste fluids resulting from the cleaning are discharged to the outside of the automated analyzer.

The suction/discharge unit 24 sucks and discharges samples, reagents, cleaning fluids and the like by control from the main control unit 10. In addition, the suction/discharge unit 24 cleans the inside of the probe 19 by use of purified water working with the pump unit 25. A water tank 26 is that in which purified water needed for cleaning the probe is kept in store. A water-amount decrease detecting switch (not illustrated) is installed in the water tank 26. In a case where the amount of purified water is smaller than a predetermined amount, the water-amount decrease detecting switch transmits a detection signal to the main control unit 10.

A light source unit 27, an optical system unit 28, and a light detecting unit 29 are constituent components of a spectrophotometer, and are used for performing an absorbance determination on the photometric cuvette of a reagent cartridge. The light source unit 27 includes a halogen lamp. The halogen lamp is always lit when and after performing an initialization check process on the automated analyzer.

The optical system unit 28 includes a rotational wavelength selecting filter, a lens and a slit. Interference filters corresponding to 12 wavelengths are mounted in a circular manner on the rotational wavelength selecting filter. The rotational wavelength selecting filter is rotated by the main control unit 10, and thus a desired interference filter is capable of being arranged on the optical axis 47. The wavelengths which the rotational wavelength selecting filter is capable of selecting are, for example, 340 nm, 380 nm, 405 nm, 450 nm, 480 nm, 508 nm, 546 nm, 576 nm, 600 nm, 660 nm, 700 nm and 800 nm.

The light detecting unit 29 includes a photodiode and an amplifier. The light detecting unit 29 is arranged on the optical axis 47 under the rotor 16. The quantity of light detected by the photodiode is transduced to a voltage, and is outputted as the voltage. The voltage is amplified by the amplifier. An analog voltage value obtained by the amplification is converted into digital data by an A/D converter 30. The resultant digital data are fetched in the main control unit 10.

Reference numeral 31 denotes a dot code reading unit. The dot code reading unit 31 optically reads the dot code printed on the label affixed to the panel 106 of one of the reagent cartridges, the panel 106 being arranged in a direction perpendicular to the optical axis 48. Data which have been read is sent to the main control unit 10.

Reference numeral 32 denotes a display/operation unit. The display/operation unit 32 includes a touch panel LCD, a START button and a STOP button. The touch panel LCD displays a message and an analysis result to a user. In addition, the user can select a process by pressing a corresponding predetermined position on the panel. The START button is used for starting the analysis operation. The STOP button is used for terminating the analysis operation in the middle.

Reference numeral 34 denotes a storage unit. The analysis result is stored, along with the patient ID and the analysis date and time, in the storage unit 34. An analysis result of the past is capable of being stored in the storage unit 34. In addition, bit information indicating whether or not an analysis operation is protected is stored in the storage unit 34. Data stored in the storage unit 34 are retained even while the power supply of the automated analyzer is off. Reference numeral 35 denotes an external printer connected to the automated analyzer through a standard interface. The external printer 35 is optional, and is used when the analysis result is intended to be printed out.

Figure 5:
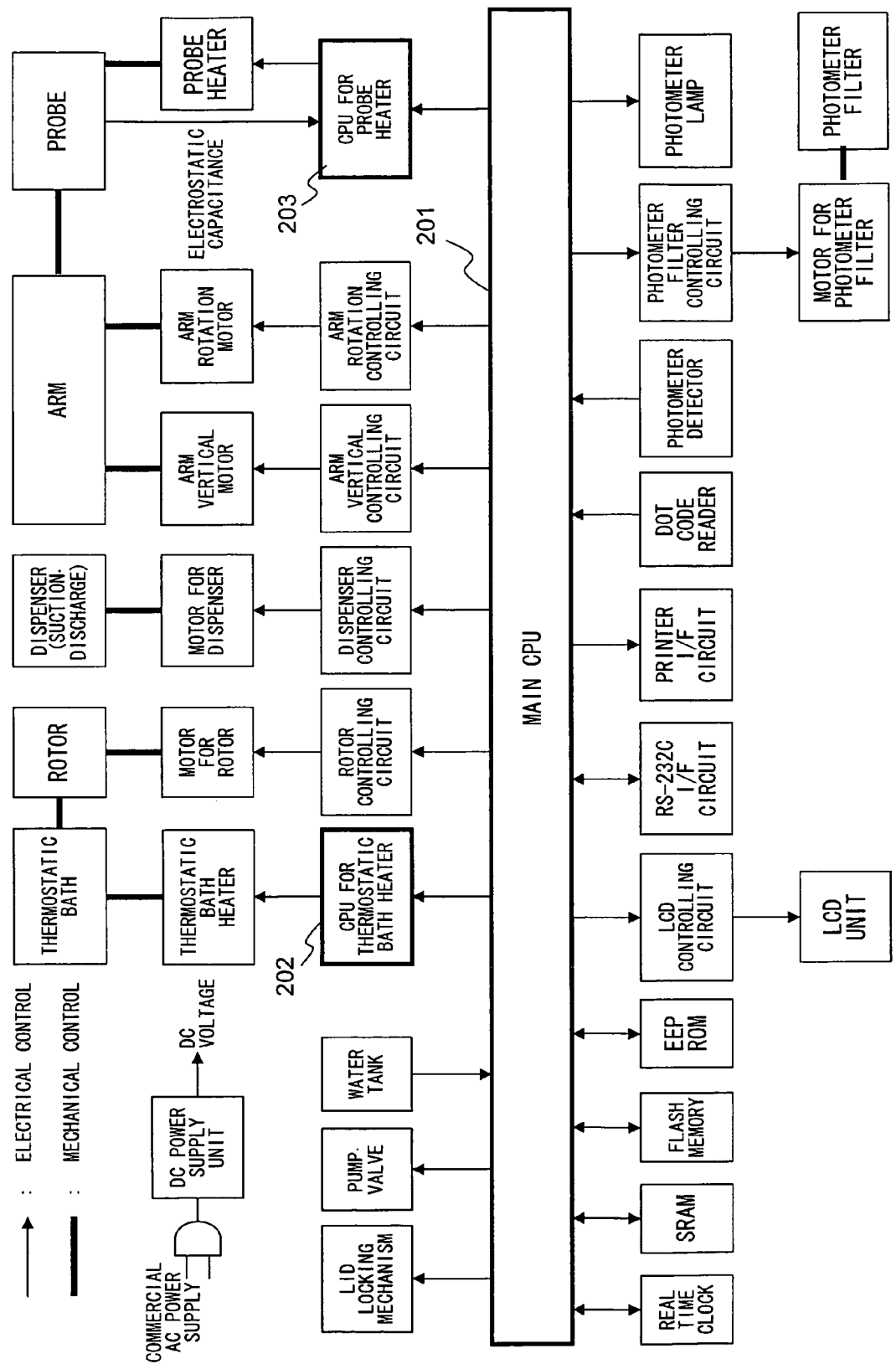
FIG. 5 is a block diagram of a control system of the automated analyzer.

FIG. 5 is a block diagram of a control system of the automated analyzer shown in FIGS. 3 and 4. A main CPU 201 shown in the figure is included in the main control unit 10. In addition, a CPU 202 for a reaction vessel heater is included in the thermostatic bath controlling unit 14, and a CPU 203 for a probe heater is included in the arm controlling unit 17.

Figure 6:
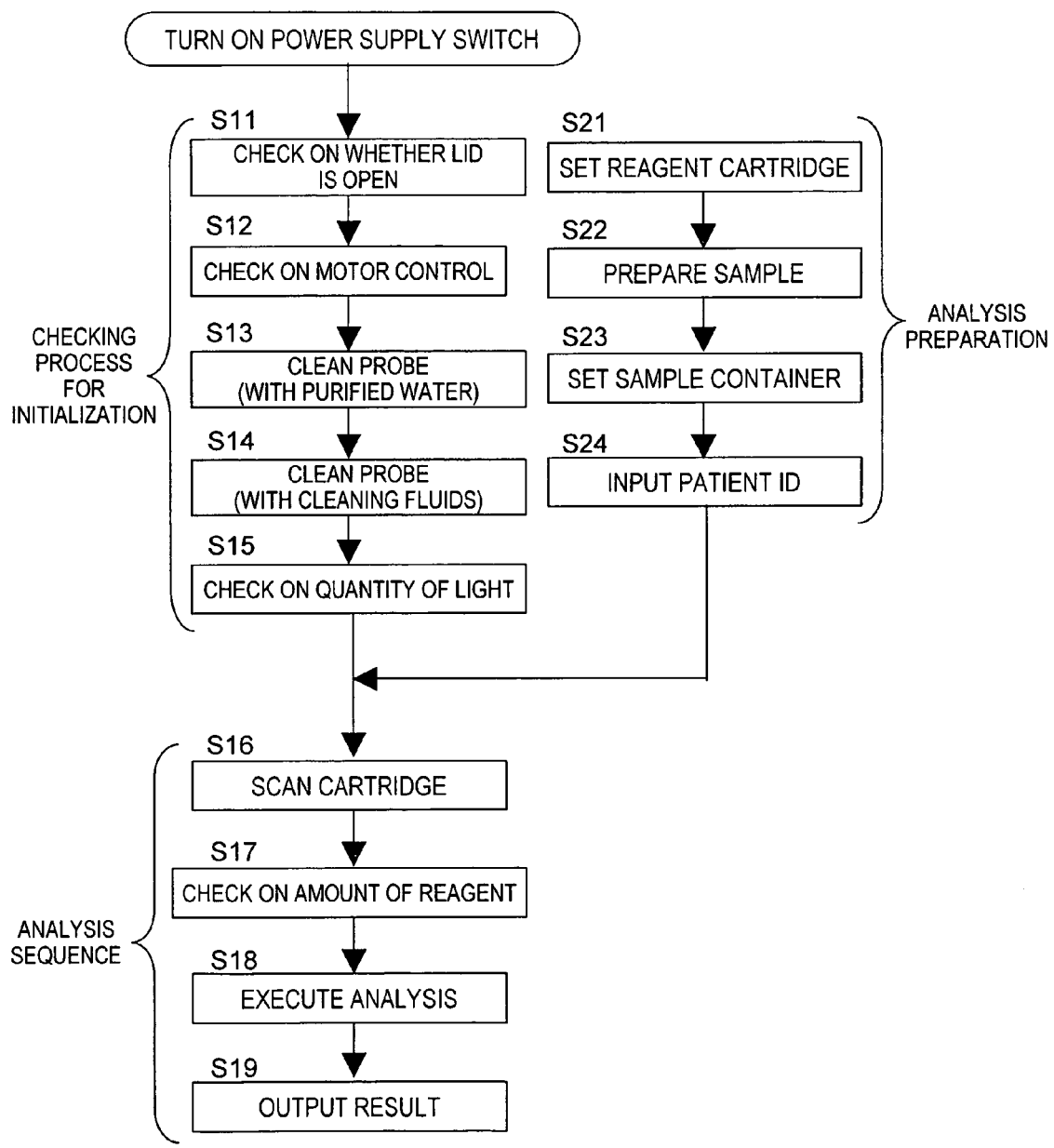
FIG. 6 is a diagram of a flow of operation of the automated analyzer according to the present invention.

Descriptions will be provided for an operation flow of the automated analyzer according to the present invention by referring to FIG. 6.

When the power supply switch is turned on, a checking process for initialization is started. With regard to the checking process for initialization, first of all, through the switch for detecting the opening of the lid, the main control unit 10 checks on whether or not the lid is closed (S11). After ascertaining that the lid is closed, the main control unit 10 further controls the lid locking mechanism, and thus locks the lid. Thereafter, the main control unit 10 checks on whether or not each of the step motors are capable of being controlled normally (S12).

Subsequently, the probe 19 is going to be cleaned with purified water. Before the cleaning, through the water-amount decrease detecting switch, the main control unit 10 checks on whether the amount of purified water in the water tank 26 is not smaller than a predetermined amount. For the cleaning of the probe 19, the main control unit 10 moves the extremity of the probe 19 to the inside of the cleaning station 23. Thereafter, the main control unit 10 controls the pump unit 25, and thus the outside of the probe 19 is cleaned by discharging water from the outer wall of the cleaning station 23. Simultaneously, the main control unit 10 controls the pump unit 25 and the suction/discharge unit 24, and thus water is discharged from the inside of the probe 19. Thereby, the inside of the probe 19 is cleaned (S13).

Subsequently, the probe 19 is going to be cleaned with three kinds of cleaning fluids. Before the cleaning, the main control unit 10 checks on the amount of each of the cleaning fluids. In other words, the main control unit 10 calculates the amount of each of the cleaning fluids from the height at which the probe 10 detects the fluid surface of the cleaning fluid, and thus ascertains that the amount of the cleaning fluid is not smaller than a predetermined amount. Thereafter, a predetermined amount of the cleaning fluid is sucked into the inside of the probe 19, and thus the inside and outside of the probe 19 is cleaned. Subsequently, the main control unit 10 moves the probe 19 to the cleaning station 23, and thus the cleaning fluid is discharged. After that, the inside and outside of the probe 19 is cleaned with purified water in the cleaning station 23. This process is performed for each of the cleaning fluids (S14). Finally, the main control unit 10 causes the halogen lamp to be lit. Thus, through the light detecting unit 29, the main control unit 10 checks on whether or not the quantity of light is not smaller than a predetermined amount (S15), when the 340 nm interference filter is set on the optical axis.

The checking process for initialization is completed with what have been described above. Preparation which the automated analyzer makes for getting itself ready for an analysis is completed. From now on, descriptions will be provided for preparation which a user makes for getting the automated analyzer ready for the analysis.

First of all, the user takes reagent cartridges 101, which correspond to an assay, out of the refrigerator, and thus sets the reagent cartridges 101 in the rotor 16 of the automated analyzer (S21). The user can arbitrarily determine in which positions in the rotor 16 the reagent cartridges 101 should be set respectively. Subsequently, from colors of sealing labels of all the reagent cartridges mounted in the rotor 16, the user determines what sample (serum, plasma, whole blood, urine and the like) should be needed for an analysis on a patient. Thus, the user pours the sample into a sample container (S22). Thereafter, the user sets the sample container in the automated analyzer (S23). Finally, the user inputs the ID of the patient from the display/analysis unit 32 (S24).

The preparation which the user makes for getting the automated analyzer ready for the analysis is completed with what have been described above. At this time, when the user presses the START button in the display/operation unit, the automated analyzer starts the analysis. Descriptions will be provided below for an analysis sequence.

First of all, the main control unit 10 refers to the bit information on protection of the analysis operation, which is stored in the storage unit 34, and thus checks on whether or not the bits have not been set up. In a case where the bits have been set up, the main control unit 10 displays the following two messages in the display/operation unit 32, and terminates the analysis operation. One of the two messages is that the analysis operation is protected. The other of the two messages is that contact to the service center is requested. Subsequently, the main control unit 10 rotates the rotor 16 through controlling the step motor 11, and thus sequentially disposes the reagent cartridges on the optical axis 48. Hence, the main control unit 10 causes the dot codes respectively of the reagent cartridges to be read by the dot code reading unit 31 (S16). Information in each of the read dot codes is stored in the RAM 33. If the aforementioned "(2) the serial number" out of the dot code information newly stored in the RAM 33 agrees with a serial number, stored in the storage unit 34, of a reagent cartridge which has been beforehand analyzed, this means that the reagent cartridge whose dot code is newly read is the same as the reagent cartridge which has already been analyzed. As a result, the main control unit 10 displays, in the display/operation unit 32, a message for requesting the cartridge to be taken out of the rotor, and terminates the execution of the analysis. Even if the reagent cartridge whose dot code is newly read has not yet been analyzed, in a case where, from information on the aforementioned "(1) the year and date of production, and the expiration date" which has been beforehand stored in the RAM 33, it is determined that the reagent cartridge has expired its effective date, the main control unit 10 similarly displays an error message in the display/operation unit 32, and terminates the execution of the analysis.

After the scanning of all of the reagent cartridges 101 is completed, the main control unit 10 is capable of identifying a sample needed for one analysis operation. Subsequently, the main control unit 10 starts checking on the amount of the sample. The main control unit 10 moves the probe 19 to a sample container from which the sample is going to be collected for the analysis, and calculates the amount of the sample from a height at which the fluid surface of the sample is detected (S17). Thereafter, the main control unit 10 moves the probe 19 to the cleaning station 23, and thus cleans the probe 19 with purified water. With regard to the execution of the analysis, the main control unit 10 determines the absorbance of each of the reagent cartridges (S18), and thus outputs a concentration-denominated result of the determination in the display/operation unit 32 (S19). Incidentally, in a case where it is determined by the cartridge scanning in step S16 that a reagent cartridge, "(12) the type of analysis" of which is classified as performance check, or a performance check cartridge, is included in the reagent cartridges set in the rotor 16, the main control unit 10 executes an analysis by use of the performance check cartridge prior to an analysis by use of any other reagent cartridge.

Figure 7:
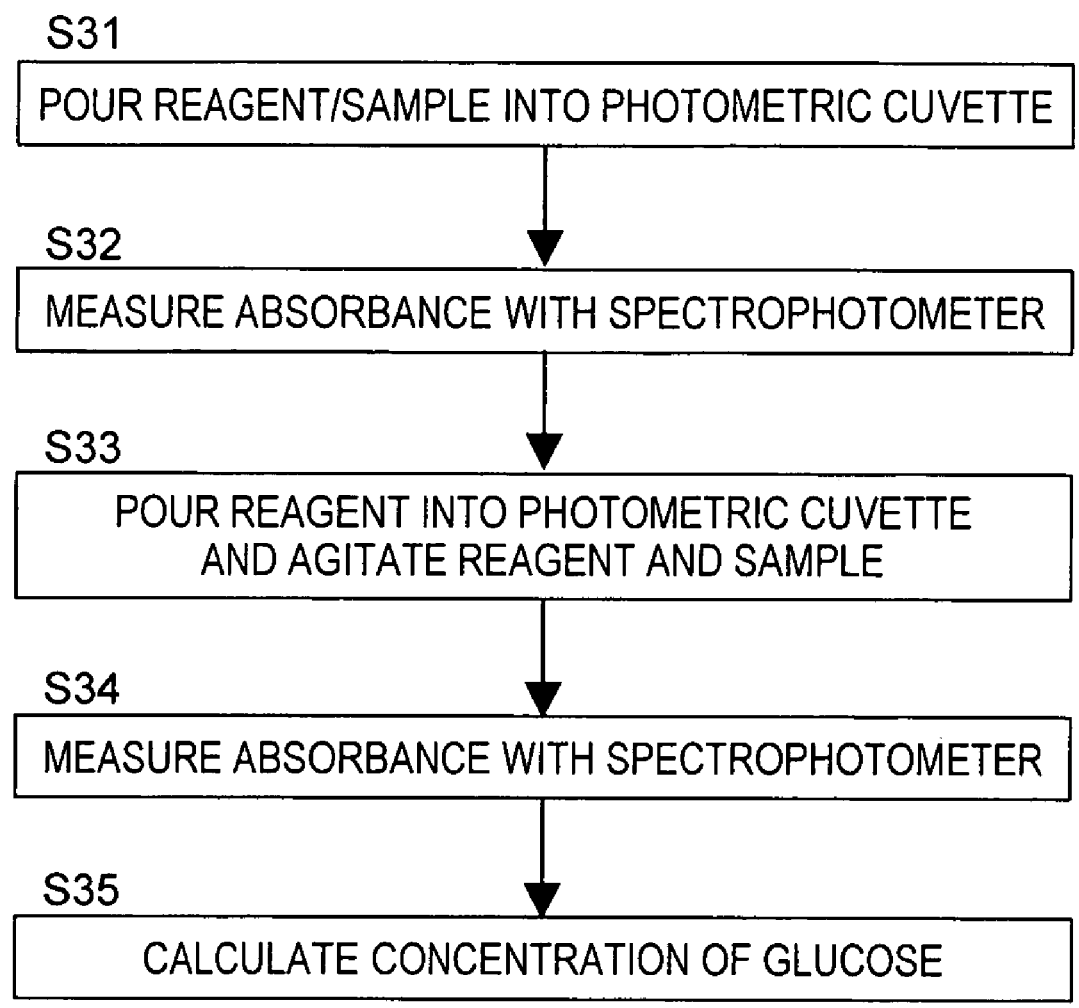
FIG. 7 is a diagram of a flow of an example of determining absorbance.
Figure 8:
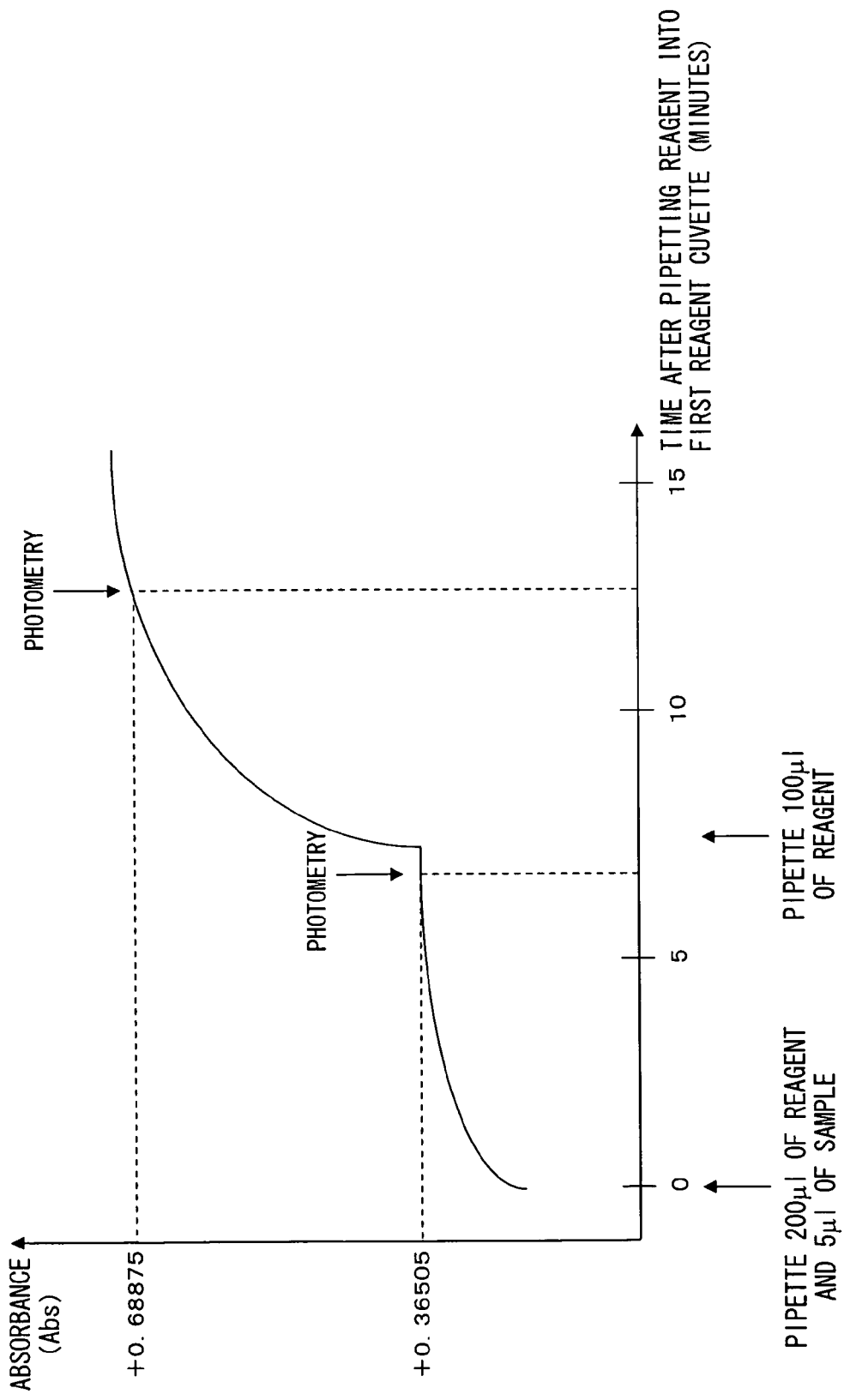
FIG. 8 is a diagram showing examples respectively of a temporal change in the absorbance, a timing for pipetting a reagent/sample, and a timing for a photometry in a case of a regular analysis.

FIG. 7 shows a flow of determining the absorbance of a reagent cartridge for a glucose (GLU) analysis as an example. In addition, FIG. 8 shows examples respectively of a temporal change in the absorbance, a timing for pipetting a reagent/sample, and a timing for a photometry.

In the case of a pre-analysis reagent cartridge, the same reagent is filled in both the first reagent cuvette and the second cuvette. The first cuvette contains 250 μl of the reagent, and the second cuvette contains 130 μl of the reagent. Both cuvettes are sealed with a sealing label. In the case of this reagent cartridge, serum is used as a sample. For this reason, the sealing label of this reagent cartridge is marked with yellow. In addition, "GLU" is typed on the sealing label of the reagent cartridge for the purpose of indicating the assay. Moreover, the following pieces of information are stored in the dot code label affixed to the reagent cartridge: "serum or plasma" as "(3) the type of a specimen needed as a sample"; "5 μl/0 minutes after the first pipetting of a reagent" as "(4) the amount of a sample needed and the timing for pipetting; "200 μl/0 minutes after the first pipetting of the reagent" as "(5) the amount of a first reagent needed and the timing for pipetting"; "100 μl/7 minutes 30 seconds after the first pipetting of the reagent" as "(6) the amount of a second reagent needed and the timing for pipetting"; "the 2-point end method" as "(8) a photometry method"; "7 minutes/12 minutes 30 seconds after the first pipetting of the reagent" as "(9) the photometric timing"; "a primary wavelength of 340 nm/a secondary wavelength of 450 nm" as "(10) a primary wavelength and a secondary wavelength for the photometry"; "concentration=200.804×(absorbance difference−(−0.05145)) mg/dl" as "(11) a transformation from the absorbance to the concentration"; and "a regular analysis" as "(12) the type of analysis." In other words, information on the analysis procedure, the process sequence and the like is stored in the dot code label affixed to each of the reagent cartridges.

In accordance with the information which has been read from the dot code label, and which is stored in the RAM 33, the main control unit 10 controls each of the units in the analyzer. First of all, the main control unit 10 pipettes the sample and the reagent which has been contained in the first reagent cuvette, into the photometric cuvette (S31). In this respect, the main control unit 10 rotates the rotor 16 in order that the center of the first reagent cuvette of the reagent cartridge may be positioned at the suction unit 44. Thereafter, the main control unit 10 rotates the arm 18, and thus moves the probe 19 to the suction unit 44. The main control unit 10 causes the probe 19 to descend in order that the extremity of the probe 19 may penetrate through the sealing label so as to be inserted in the first reagent cuvette. The probe 19 sucks 200 µl of the reagent from the first reagent cuvette. Subsequently, the main control unit 10 refers to the information on the type of the specimen as the sample. The information is stored in the RAM 33. In this case, the information on the type of the specimen is "serum or plasma." Since the specimen type and the sample container uniquely correspond to each other, the main control unit 10 is capable of identifying the sample container 21a containing the serum. The main control unit 10 moves the probe 19 to a position where the serum sample container 21a is located. Thereafter, the probe 19 sucks 5 µl of the serum from the serum sample container. Subsequently, the main control unit 10 rotates the rotor 16 in order that the center of the photometric cuvette may be positioned at the suction/discharge unit 45. After that, the main control unit 10 moves the probe 19 to the suction/discharge unit 45, and causes the probe 19 to descend there. After the extremity of the probe 19 penetrates through the sealing label so that the extremity is inserted in the photometric cuvette, the reagent and the sample are discharged into the photometric cuvette. The mixed fluid of the reagent and the sample contained in the photometric cuvette is sucked and discharged by the probe 19, and thereby is agitated. Thereafter, the main control unit 10 moves the probe 19 to the cleaning station 23, and the inside and outside of the probe 19 is cleaned with purified water.

Figure 9:
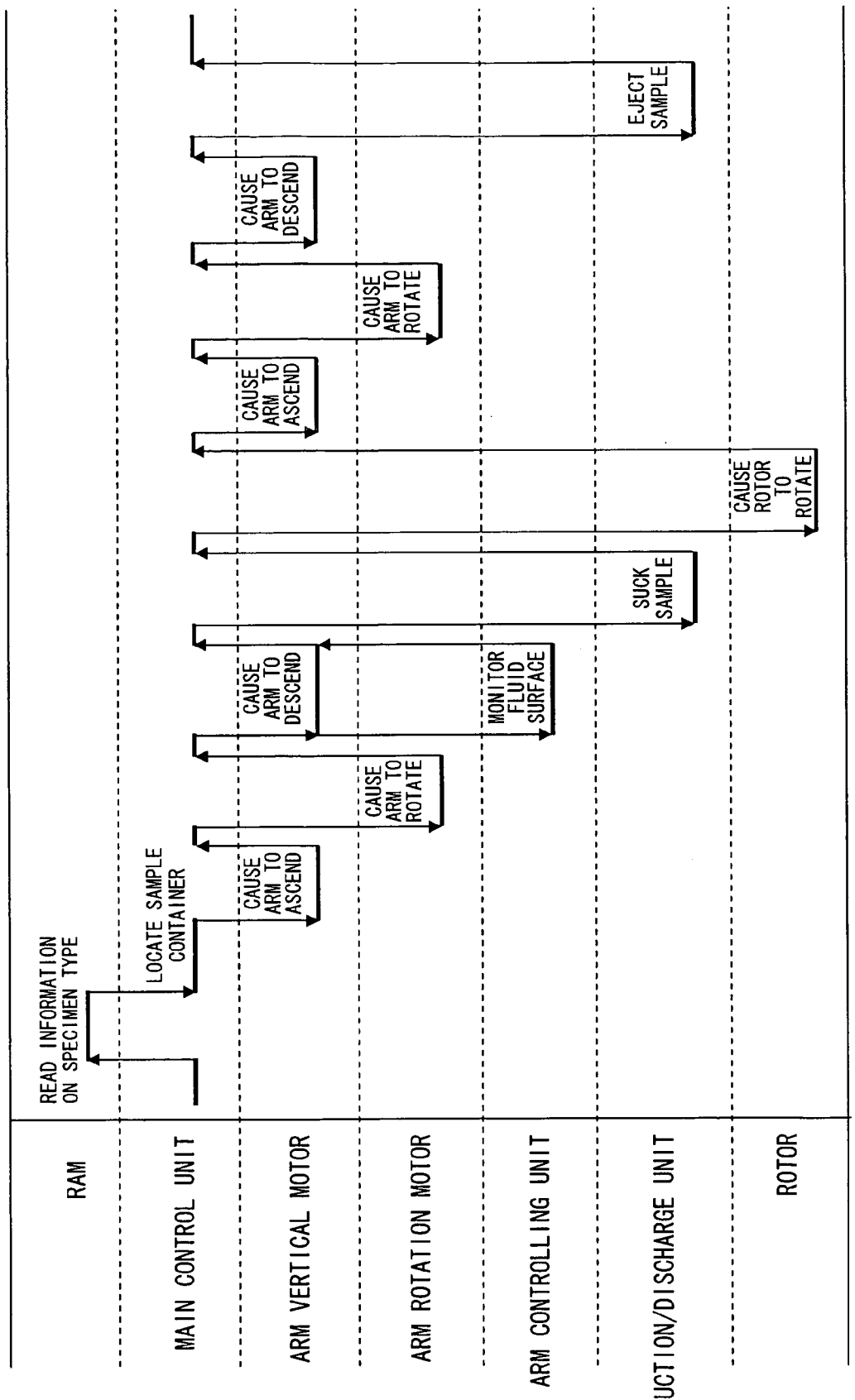
FIG. 9 is a diagram showing an example of a sequence of controlling each piece of the hardware.

FIG. 9 shows an example of a sequence of controlling each piece of the hardware from the reference to the RAM 33 through the discharge of the reagent and the sample. First of all, the main control unit 10 refers to the RAM 33, and thus reads the information on the specimen type therefrom. On the basis of the information on the specimen type, the main control unit 10 locates the sample container. In the case of this example, the main control unit 10 locates the sample container 21a. Subsequently, the main control unit 10 shifts itself to an operation for causing the probe 19 to suck the sample from the sample container 21a. To this end, the main control unit 10 controls the step motor 13 for vertical motion, and thus causes the arm 18 to ascend. Thereafter, the main control unit 10 controls the rotation controlling step motor 12, and thus rotates the arm 18 with a predetermined angle. Hence, the main control unit 10 positions the probe 19 above the sample container 21a. After that, the main control unit 10 controls the step motor 13 for vertical motion, and causes the arm 18 to descend. When the extremity of the probe 19 enters the sample contained in the sample container 21a sufficiently deeply, the main control motor 10 stops the descending motion of the arm 18. At this time, the arm control unit 17 detects change in electrostatic capacitance between the probe 19 and the ground potential, and thus monitors the fluid surface. Subsequently, the main control unit 10 controls the suction/discharge unit 24, and thus a predetermined amount of the sample is sucked by the probe 19 from the sample container 21a.

Thereafter, the main control unit 10 controls the step motor 11, and thus rotates the rotor 16. Hence, the main control unit 10 positions the center of the photometric cuvette 102 of the reagent cartridge 101 to be used for the analysis at the suction/discharge unit 45. Incidentally, this rotor 16 may be rotationally moved at the same time as the sample is sucked by the probe 19 from the sample container 21a.

On the other hand, the main control unit 10 controls the step motor 13 for vertical motion, and thus causes the arm 18 to ascend. Hence, the main control unit 10 extracts the probe 19 from the sample container 21a, after the suction of the sample by the probe 19 is completed. Subsequently, the main control unit 10 controls the rotation controlling step motor 12, and thus causes the arm 18 to rotate, hence positioning the probe 19 above the suction/discharge unit 45. Thereafter, the main control unit 10 controls the step motor 13 for vertical motion, and thus causes the arm 18 to descend towards the photometric cuvette 102 of the reagent cartridge 101. Hence, the main control unit 10 causes the extremity of the probe 19 to be inserted in the photometric cuvette while breaking the sealing label. When the extremity of the probe 19 enters the inside of the photometric cuvette 102, the main control unit stops the arm 18's descending. Subsequently, the main control unit 10 controls the suction/discharge unit 24, and thus causes the sucked reagent and sample to be discharged from the extremity of the probe 19 to the inside of the photometric cuvette 102.

7 minutes after the first pipetting of the reagent, the main control unit 10 controls each of the units in the analyzer, and thus determines the absorbance of the photometric cuvette containing the sample (S32). In this respect, the main control unit 10 rotates the rotor 16 in order that the center of the photometric cuvette may be positioned at the optical axis 47. Thereafter, the main control unit 10 causes the spectrophotometer to determine the absorbance with the primary wavelength of 340 nm and the secondary wavelength of 450 nm. The spectrophotometer is configured of the light source unit 27, the optical system unit 28 and the light detecting unit 29. In the case of the example shown in FIG. 8, the result of the determination is expressed with:

Absorbance=+0.36505 Abs 7 minutes 30 seconds after the first pipetting of the reagent, the main control unit 10 controls each of the units in the analyzer, and thus causes the reagent contained in the second reagent cuvette to be pipetted into the photometric cuvette (S33). In this respect, the main control unit 10 rotates the rotor 16 in order that the center of the second reagent cuvette may be positioned at the suction unit 46. Subsequently, the main control unit 10 moves the probe 19 to the suction unit 46, and thus causes the 100 µl of the reagent to be sucked from the second reagent cuvette. After that, the main control unit causes the probe 19 to ascend. Thereafter, the main control unit 10 rotates the rotor 16 in order that the center of the photometric cuvette may be positioned at the suction/discharge 45. Subsequently, the main control unit 10 rotates the arm 18, and thus moves the probe 19 to the suction/discharge unit 45, hence causing the reagent to be discharged into the photometric cuvette. Subsequently, the main control unit 10 causes the probe 19 to suck and discharge the mixed fluid of the reagent and the sample contained in the photometric cuvette, and thus the mixed fluid of the reagent and the sample is agitated. Thereafter, the main control unit 10 moves the probe to the cleaning station 23, and thus the inside and outside of the probe 19 is cleaned with purified water.

12 minutes 30 seconds after the first pipetting of the reagent, the main control unit 10 controls each of the units in the analyzer, and thus determines the absorbance of the photometric cuvette containing the mixed fluid of the reagent and the sample (S34). In this respect, the main control unit 10 rotates the rotor 16 in order that the center of the photometric cuvette of the reagent cartridge may be positioned at the optical axis 47. Thereafter, the main control unit 10 causes the spectrophotometer to determine the absorbance with the primary wavelength of 340 nm and the secondary wavelength of 450 nm. The spectrophotometer is configured of the light source unit 27, the optical system unit 28 and the light detecting unit 29. In the case of this example, from FIG. 9, the result of the determination is expressed with:

Absorbance=+0.68875 Abs

The difference between the results of the two determinations is calculated as follows:

+0.68875−(+0.36505)=+0.32370 Abs

This difference is substituted for the transformation from the absorbance to the concentration which is stored in the RAM 33. The transformation is expressed with:

concentration=200.804× (absorbance difference−(−0.05145))mg/dl

The substitution brings about a result that the concentration of the glucose is equal to "75.3 mg/dl" (S35).

After the main control unit 10 finishes determining the concentration as the assay on the first reagent cartridge, the main control unit 10 sequentially determines the concentrations respectively of all the reagent cartridges from the ensuing reagent cartridge to the last reagent cartridge, which are set in the rotor 16, as the assays set up for the reagent cartridges. In this respect, it is desirable that reagent cartridges for which to use the same type of specimens as the respective samples should be collectively determined. In a case where, for example, 20 reagent cartridges for which to use serum as the respective samples and 10 reagent cartridges for which to use urine as the respective samples are mounted on the automated analyzer, the concentrations respectively of the 20 reagent cartridges for serum are sequentially determined first, and the concentrations respectively of the 10 reagent cartridges for urine are sequentially determined later. The main control unit 10 applies information on each of the reagent cartridges, which has been obtained by the cartridge scanning, to an algorithm concerning the analysis sequence. Thus, the main control unit 10 schedules the analyses.

The analysis result are displayed in the display/operation unit 32. The analysis result along with the patient ID, the date and time, and the serial number of the used reagent cartridge is stored in the storage unit 34. In a case where an external printer 35 is connected to the automated analyzer, the analysis result is printed out, and thus terminates the operation normally. Analysis data of the past can be stored in the storage unit 34. For this reason, a piece of the analysis data of the past can be selected from the display/operation unit 32, and thus can be always printed out through the external printer.

Figure 10:
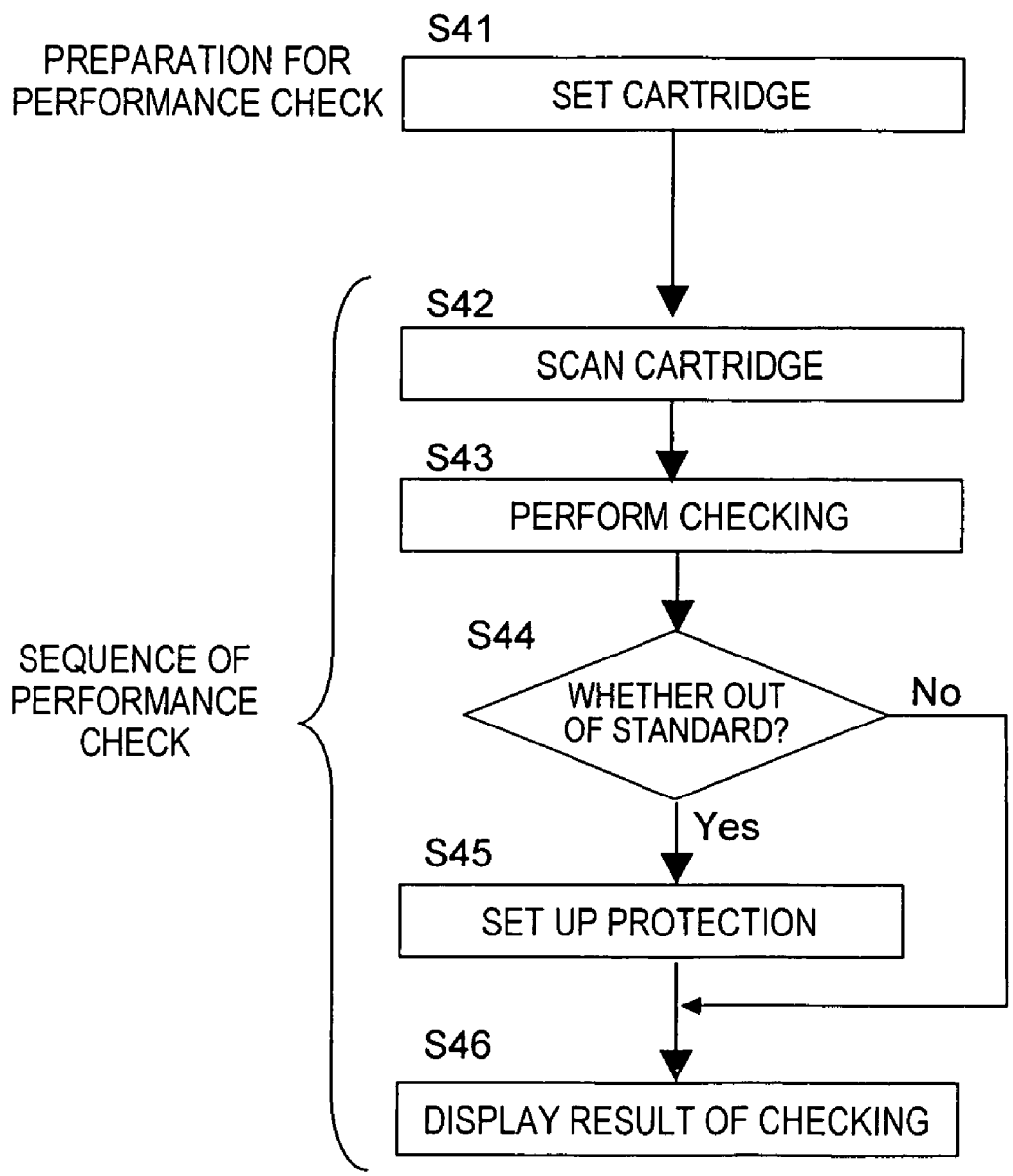
FIG. 10 is a diagram of a flow of performance check according to the present invention.
Figure 11:
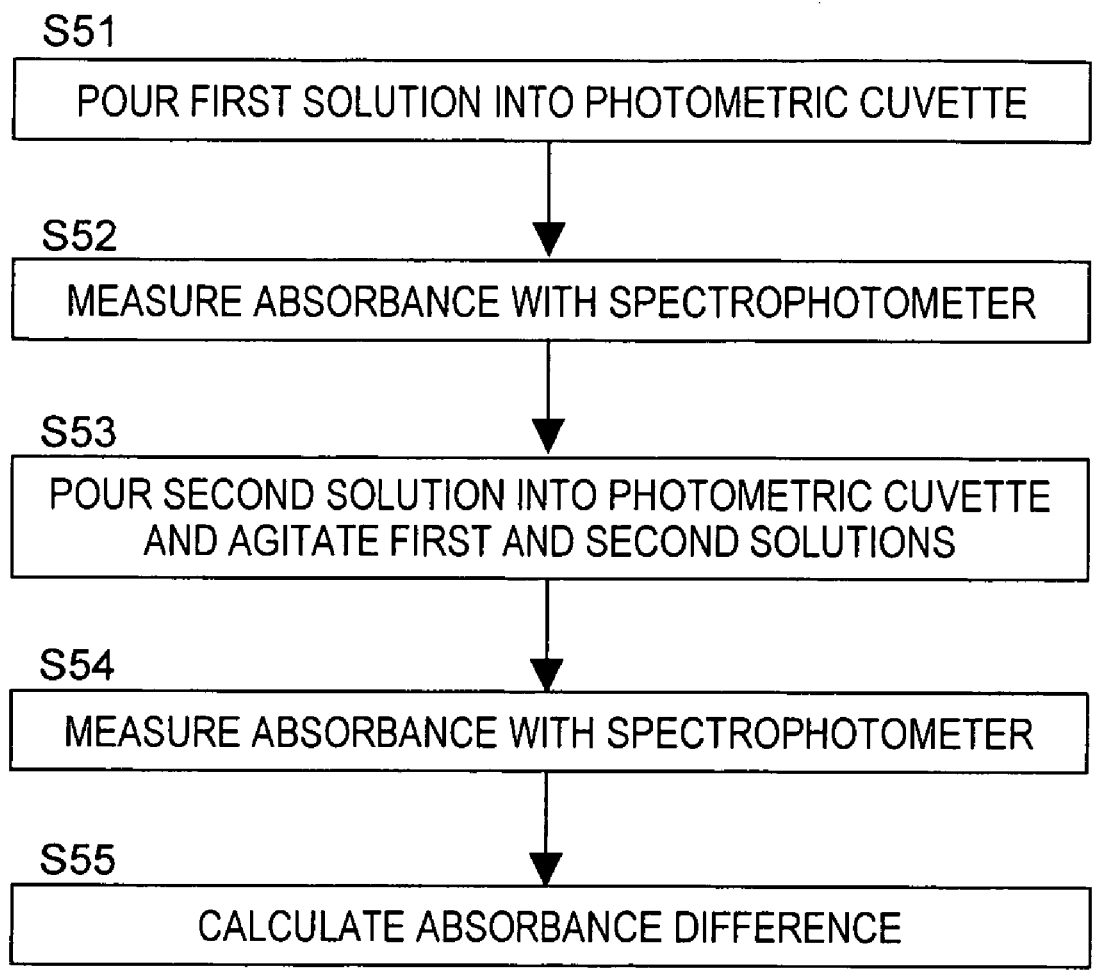
FIG. 11 is a diagram of a flow of an example of determining the absorbance.

Descriptions will be provided below for preparation which a user makes for the performance check and a sequence of the performance check by referring to FIGS. 10 and 11.

First of all, the user takes one performance check cartridge on which "CHECK1" is typed, and another performance check cartridge on which "CHECK2" is typed, out of the refrigerator. Subsequently, the user sets the two performance check cartridges in the rotor 16 (S41). The user can arbitrarily determine in which positions in the rotor 16 the performance check cartridges should be set respectively. In this respect, when the user presses the START button in the display/operation unit, the performance check is started. Descriptions will be provided below for a sequence for the performance check.

First of all, the main control unit 10 rotates the rotor 16 through controlling the step motor 11, and thus sequentially disposes the performance check cartridges on the optical axis 48. Hence, the main control unit 10 causes the dot codes respectively of the performance check cartridges to be read by the dot code reading unit 31 (S42). Information in each of the read dot codes is stored in the RAM 33. If the aforementioned "(2) the serial number" out of the dot code information newly stored in the RAM 33 agrees with a serial number stored in the storage unit 34, of a reagent cartridge which has been beforehand analyzed, this means that the performance check cartridge whose dot code is newly read is the same that the performance check cartridge which has already been analyzed. As a result, the main control unit 10 displays, in the display/operation unit 32, a message for requesting the cartridge to be taken out of the rotor, and terminates the execution of the performance check. Even if the reagent cartridge whose dot code is newly read has not yet been analyzed, in a case where, from information on the aforementioned "(1) the year and date of production and the expiration date" which has been beforehand stored in the RAM 33, it is determined that the performance check cartridge has expired its effective date, the main control unit 10 similarly displays an error message in the display/operation unit 32, and terminates the execution of the analysis.

Figure 12:
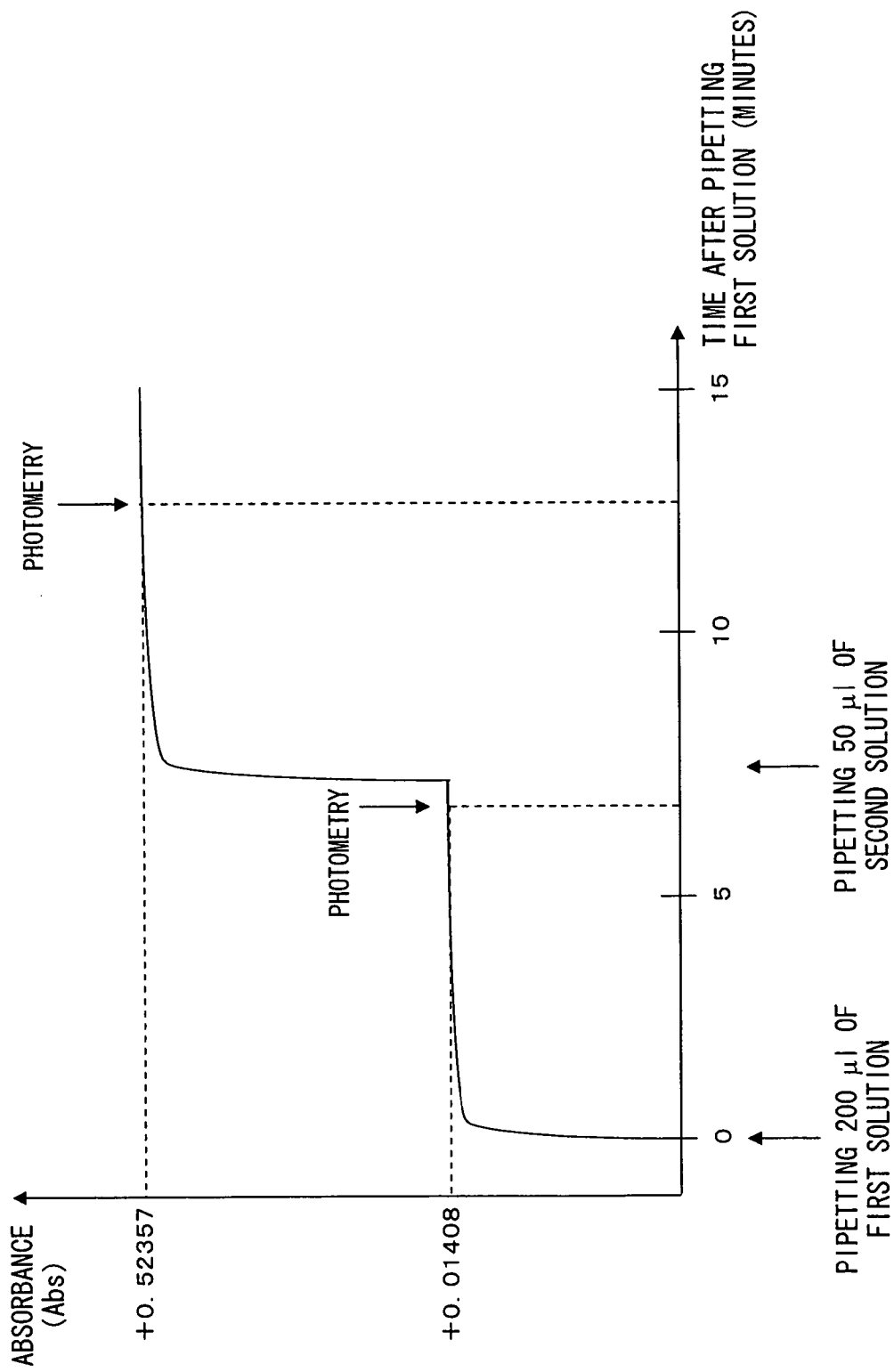
FIG. 12 is a diagram showing examples respectively of a temporal change in the absorbance, a timing for pipetting a reagent/a sample, and a timing for a photometry in a case of the performance check.

With regard to the execution of the performance check, the absorbance of each of the performance check cartridges is determined (S43). FIG. 11 shows a flow of determining the absorbance of the performance check cartridge, on which "CHECK1" is typed, as an example. In addition, FIG. 12 shows examples respectively of a temporal change in the absorbance, a timing for pipetting a reagent/sample, and a timing for a photometry.

The following pieces of information are stored in the dot code label affixed to the performance check cartridge: "200 μl/0 minutes after the first pipetting of the reagent" as "(5) the amount of a first reagent needed and the timing for pipetting"; "50 μl/7 minutes 30 seconds after the first pipetting of the reagent" as "(6) the amount of a second reagent needed and the timing for pipetting"; "the 2-point end method" as "(8) a photometry method"; "7 minutes/12 minutes 30 seconds after the first pipetting of the reagent" as "(9) the photometric timing"; "a primary wavelength of 405 nm/a secondary wavelength of 800 nm" as "(10) a primary wavelength and a secondary wavelength for the photometry"; "performance check 1" as "(12) the type of analysis"; "0.55 Abs" as "(12) the upper limit value of the absorbance difference"; and "0.45 Abs" as "(14) the lower limit value of the absorbance difference. In other words, information on the check procedure, the criteria and the like is stored in the dot code label affixed to each of the reagent cartridges.

In accordance with the information which has been read from the dot code label, and which is stored in the RAM 33, the main control unit 10 controls each of the units in the analyzer. First of all, the main control unit 10 pipettes a solution, which is contained in the first reagent cuvette, into the photometric cuvette (S51). In this respect, the main control unit 10 rotates the rotor 16 in order that the center of the first reagent cuvette of the reagent cartridge may be positioned at the suction unit 44. Thereafter, the main control unit 10 rotates the arm 18, and thus moves the probe 19 to the suction unit 44. The main control unit 10 causes the probe 19 to descend in order that the extremity of the probe 19 may penetrate through the sealing label so as to be inserted in the first reagent cuvette. The probe 19 sucks 200 μl of the solution from the first reagent cuvette. Subsequently, the main control unit 10 rotates the rotor 16 in order that the center of the photometric cuvette may be positioned at the suction/discharge unit 45. Thereafter, the main control unit 10 moves the probe 19 to the suction/discharge unit 45, and causes the probe 19 to descend there. After the extremity of the probe 19 penetrates through the sealing label so that the extremity is inserted in the photometric cuvette, the solution is discharged into the photometric cuvette. Thereafter, the main control unit 10 moves the probe to the cleaning station 23, and the inside and outside of the probe 19 is cleaned with purified water.

7 minutes after the first pipetting of the solution, the main control unit 10 controls each of the units in the analyzer, and thus determines the absorbance of the photometric cuvette containing the solution (S52). In this respect, the main control unit 10 rotates the rotor 16 in order that the center of the photometric cuvette of the performance check cartridge may be positioned at the optical axis 47. Thereafter, the main control unit 10 causes the spectrophotometer to determine the absorbance with the primary wavelength of 340 nm and the secondary wavelength of 800 nm. The spectrophotometer is configured of the light source unit 27, the optical system unit 28 and the light detecting unit 29. In the case of the example shown in FIG. 12, the result of the determination is expressed with:

$$\text{Absorbance} = +0.01408 \text{ Abs}$$

7 minutes 30 seconds after the first pipetting of the solution, the main control unit 10 controls each of the units in the analyzer, and thus causes the solution contained in the second reagent cuvette to be pipetted into the photometric cuvette (S53). In this respect, the main control unit 10 rotates the rotor 16 in order that the center of the second reagent cuvette of the performance check cartridge may be positioned at the suction unit 46. Subsequently, the main control unit 10 moves the probe 19 to the suction unit 46, and thus causes the 50 μl of the solution to be sucked from the second reagent cuvette. After that, the main control unit 10 causes the probe 19 to ascend. Thereafter, the main control unit 10 rotates the rotor 16 in order that the center of the photometric cuvette may be positioned at the suction/discharge 45. Subsequently, the main control unit 10 rotates the arm 18, and thus moves the probe 19 to the suction/discharge unit 45, hence causing the solution to be discharged into the photometric cuvette. After that, the main control unit 10 causes the probe 19 to suck and discharge the mixed fluid of the first solution and the second solution contained in the photometric cuvette, and thus the mixed fluid of the two solutions is agitated. Thereafter, the main control unit 10 moves the probe to the cleaning station 23, and thus the inside and outside of the probe 19 is cleaned with purified water.

12 minutes 30 seconds after the first pipetting of the solution, the main control unit 10 controls each of the units in the analyzer, and thus determines the absorbance of the photometric cuvette containing the mixed fluid of the first solution and the second solution (S54). In this respect, the main control unit 10 rotates the rotor 16 in order that the center of the photometric cuvette of the reagent cartridge may be positioned at the optical axis 47. Thereafter, the main control unit 10 causes the spectrophotometer to determine the absorbance with the primary wavelength of 340 nm and the secondary wavelength of 800 nm. The spectrophotometer is configured of the light source unit 27, the optical system unit 28 and the light detecting unit 29. In the case of this example, from FIG. 12, the result of the determination is expressed with:

$$\text{Absorbance} = +0.52357 \text{ Abs}$$

The difference between the results of the two determinations is calculated as follows (S55):

$$+0.52357 - (+0.01408) = +0.50949 \text{ Abs}$$

After the main control unit 10 finishes determining the absorbance of the cartridge on which "CHECK1" is typed, the main control unit 10 determines the absorbance of the cartridge on which "CHECK2" is typed.

The rest of the sequence of the performance check will be described by referring to FIG. 10 again. After the main control unit 10 finishes determining the absorbance of each of the two performance check cartridges, the main control unit 10 compares the measured value of the difference between the two absorbances with each of the upper and lower limit values (threshold values) (S44).

In this respect, in a case where the measured value of the difference between the two absorbances is beyond any one of the upper and lower limit values specified by the dot code, which have been read from the rear panel of the performance check cartridge, the main control unit 10 sets up bits on the analysis operation protection which are stored in the storage unit 34 (S45). Subsequently, the main control unit 10 displays the measured value of the difference between the two absorbances in the display/operation unit 32 (S46) along with the following messages: that the analysis operation are protected and that contact to the service center is requested. In a case where the measured value of the difference between the two absorbances falls within the range between the upper and lower limit values (threshold values) specified by the dot code, which have been read from the rear panel of the performance check cartridge, the main control unit 10 displays the following two things in the display/operation unit 32 (S46). One of the two things is a message that the result of the performance check is OK. The other of the two things is the measured value of the difference between the two absorbances.

The result of the performance check along with the patient ID, the date and time, and the serial number of the used performance check cartridge is stored in the storage unit 34. In a case where the external printer 35 is connected to the automated analyzer, the check result can be printed out. Results of the performance checks of the past can be stored in the storage unit 34. For this reason, any result of the performance check of the past can be selected from the display/operation unit 32, and thus can be always printed out through the external printer.

In the case of the present example, the acceptability is evaluated only through comparing the measured value of the difference between the two absorbances with each of the upper and lower limit values. Instead, the acceptability may be evaluated through comparing the ratio of measured values of differences among absorbances with each of the corresponding upper and lower limit values (threshold values). The proportionality of absorbance to concentration is importance in a quantitative analysis based on the Lambert-Beer's law. Stray light in the spectrophotometer and the like are factors which makes the proportionality of absorbance worse. The proportionality of absorbance can be evaluated through calculating the ratio among absorbances. For example, in the case of the present example, when the measured value of the absorbance difference in the cartridge on which "CHECK2" is typed is equal to +1.03243 Abs, the ratio of the absorbance difference is equal to 2.026. Thus, the acceptability can be evaluated through comparing the ratio of the absorbance difference and each of the upper and lower limit values. The upper and lower limit values (threshold values) are stored in the dot code.

In addition, the performance check cartridges may be of one type or of more than two types. In the case where the performance check cartridges are of more than two types, a plurality of ratios of the absorbance differences can be obtained. The acceptability can be evaluated by setting up the upper and lower limit values for each of the ratios of the absorbance differences.

Furthermore, in the case of the present example, the regular analysis and the performance check are carried out separately. However, the regular analysis and the performance check can be carried out simultaneously. In a case where, for example, two cartridges specialized for performance check are mounted in the rotor (positions in the rotor are arbitrary), at maximum 38 reagent cartridges for regular analyses can be mounted in the rotor. This makes it possible to consecutively carry out the regular analyses right after the performance check. In this case, as described above, it is learned, through the pre-analysis cartridge scanning, that the performance check cartridges are present among the reagent cartridges set in the rotor 16. For this reason, the main control unit 10 specifies the performance check cartridges as cartridges to be analyzed first, and carries out the analysis using the performance check cartridges prior to the analyses using the other reagent cartridges. The result of the performance check is displayed in parallel with the results of the regular analyses. In a case where the result of the performance check is NG, the main control unit 10 displays a message concerning the fact in the display/operation unit 32, and thereafter terminates the regular analyses. The present example makes it possible to cut the time needed for carrying out only the performance check.

Use of the cartridges specialized for the performance check as in the present example makes it possible to simply check on the performance of the entire system, which cannot be evaluated by conventional types of mechanical checks or electrical checks, through a method similar to that with which the regular analysis operation is performed.

What is claimed is:

1. An automated analyzer comprising:
   a cartridge holding unit which enables holding of at least one of a plurality of performance check cartridges, each performance check cartridge including a first reagent cuvette in which a first reagent is filled, a second reagent cuvette in which a second reagent is filled, a photometric cuvette, and an information recording unit in which process information including analysis conditions and upper and lower absorbance limit values for determining absorbance is recorded, respectively;
   a probe which pipettes the first and second reagents into the photometric cuvette;
   an optical measuring unit which includes a light source, a wavelength selecting unit and a light detector, and which determines the absorbance of the photometric cuvette of the performance check cartridge;
   an information reading unit which reads the process information recorded in the information recording unit of the performance check cartridge; and
   a control unit which controls the probe and the optical measuring unit depending on the process information read by the information reading unit, which calculates difference information of absorbances of a solution of the first reagent and a mixture of the first and second reagents in the photometric cuvette of a respective performance check cartridge on the basis of an output from the optical measuring unit, and which determines whether or not the calculated difference information of absorbances is within a predetermined tolerance by comparing the calculated difference information of absorbances for the respective performance check cartridge with the upper and lower limit values read by the information reading unit for the respective performance check cartridge.

2. The automated analyzer according to claim 1, wherein the control unit compares the difference information of absorbances with the upper and lower absorbance limit values for each of a plurality of performance check cartridges.

3. The automated analyzer according to claim 2, wherein the control unit compares an absorbance a ratio of the difference information of absorbances for two performance check cartridges with the upper and lower absorbance limit values.

4. The automated analyzer according to claim 1, further comprising a display unit,
   wherein, when the calculated difference information of absorbance is out of the predetermined tolerance, the control unit provides a warning which is displayed in the display unit.

5. The automated analyzer according to claim 1, wherein the control unit calculates the difference information of absorbances for at least two performance check cartridges and determines whether or not each of the calculated difference information of absorbances is within the predetermined tolerance of the respective performance check cartridge.

6. The automated analyzer according to claim 1, wherein the information recording unit stores the process information as a code on a respective performance check cartridge, and the information reading unit is a code reader.

7. The automated analyzer according to claim 1, wherein the cartridge holding unit is capable of rotating, and further comprising a driving unit for driving the cartridge holding unit to rotate.

* * * * *